United States Patent [19]

Gruffaz et al.

[11] 4,281,176

[45] Jul. 28, 1981

[54] PREPARATION OF ETHYL CARBOXYLATES

[75] Inventors: Max Gruffaz, La Mulatiere; Odile Micaelli, Lyons, both of France

[73] Assignee: Rhone-Poulenc Industries, Paris, France

[21] Appl. No.: 3,814

[22] Filed: Jan. 16, 1979

[30] Foreign Application Priority Data

Jan. 16, 1978 [FR] France ................................ 78 01570
Nov. 22, 1978 [FR] France ................................ 78 33770

[51] Int. Cl.$^3$ .......................... C07C 67/04; C11C 3/00
[52] U.S. Cl. ................................... 560/247; 260/405.5; 260/405; 260/410; 560/1; 560/96; 560/103; 560/204; 560/205; 560/219; 560/226; 260/410.9 R
[58] Field of Search ............... 560/247, 241, 103, 205, 560/219, 226; 260/408, 410.9

[56] References Cited

U.S. PATENT DOCUMENTS

| | | | |
|---|---|---|---|
| 2,006,734 | 7/1935 | Edlund | 560/247 |
| 2,224,809 | 12/1940 | Coleman | 560/247 |
| 2,551,643 | 5/1951 | Seger | 560/241 |
| 3,474,131 | 10/1969 | Schmerling | 560/247 |
| 3,907,873 | 9/1975 | Wight | 560/241 |
| 4,048,220 | 9/1977 | Cardenas | 560/241 |

FOREIGN PATENT DOCUMENTS

447461 3/1948 Canada .................................. 560/241

OTHER PUBLICATIONS

Roberts, J. Chem. Soc., Perkins Trans, 2, pp. 1183–1190, (1976).
Morin, Ind. & Eng. Chem., 43, pp. 1596–1600 (1951).
Battacharyya, J. Appl. Chem. 13, pp. 544–547, (1963).
Fieser, "Reagents for Organic Synthesis", pp. 1109–1111, (1967).
Moelwyn-Hughes, "Physical Chemistry", 2nd Ed., pp. 880–881, (1961).

*Primary Examiner*—Natalie Trousof
*Assistant Examiner*—Michael Shippen
*Attorney, Agent, or Firm*—Burns, Doane, Swecker & Mathis

[57] ABSTRACT

Carboxylic acids are esterified with ethylene gas, to effect the formation of ethyl esters, by acid catalysis in the presence of at least one dissociating, inert and stable solvent which increases the acidity of the reaction medium.

19 Claims, No Drawings

PREPARATION OF ETHYL CARBOXYLATES

BACKGROUND OF THE INVENTION

1. Field of the Invention

The present invention relates to a novel process for the preparation of organic esters, and, more especially, relates to a process for the preparation of ethyl carboxylates by reacting a carboxylic acid with ethylene.

2. Description of the Prior Art

It has long been known that carboxylic acids react with and are esterified by olefins in the presence of acid catalysts. Although the advantages of this method for the synthesis of esters, compared to the conventional processes utilizing alcohols and inorganic acid catalysts in the liquid phase, were quickly recognized, such method has nevertheless remained a laboratory curiosity, notably in an ethyl carboxylate synthesis, because of certain difficulties encountered in the course of the reaction.

In fact, as has been earlier reported [*Ind. & Eng. Chem.*, 1951, 43, pages 1,596–1,600 and *J. appl. Chem.*, 1963, pages 544–547], ethylene can only be esterified by a carboxylic acid, in the presence of an acid catalyst, under extremely severe conditions. These extremely harsh conditions, moreover, promote various secondary reactions, in particular polymerization reactions, which reactions compete with the esterification at the expense of the yield of the desired ester.

SUMMARY OF THE INVENTION

Accordingly, it is a major object of the present invention to provide an improved process, affording enhanced yields, for the preparation of ethyl esters by reacting ethylene with organic carboxylic acids.

Another object of the invention is to provide for the esterification of ethylene, which esterification is known to be difficult, under much less severe conditions than those heretofore employed, and thus to render the process more economical on an industrial scale.

According to the present invention, it has now surprisingly been shown that it is possible to facilely react ethylene with at least one carboxylic acid, in the liquid phase, and in the presence of at least one acid catalyst, to remarkably provide ethyl esters in good yield, by conducting the reaction in a certain type of solvent, which is defined below, under relatively mild conditions, with the result that the process can easily be scaled up to an industrial level.

It too has surprisingly and unexpectedly been shown, consistent herewith, that the necessary combination of the use of an acid catalyst and the presence of the noted particular type of solvent makes it possible to achieve this advance in the art, and, in contrast to the known prior art, enables successful esterification of a variety of carboxylic acids.

DETAILED DESCRIPTION OF THE INVENTION

More particularly, it has now been found that it is possible to prepare ethyl esters from ethylene by reacting ethylene, in the liquid phase, with a mixture essentially comprising a carboxylic acid, an acid catalyst, and at least one dissociating solvent which increases the acidity of the reaction medium. Moreover, the solvent must be stable under the reaction conditions, in particular it must be stable in an acid medium and at high temperatures. Furthermore, the solvent must be inert under the reaction conditions; it must not itself react with either the reactants or the reaction products. It has been found that non-basic organic compounds having a dielectric constant on the order of at least 25 are particularly suitable for carrying out the process according to the invention. By way of examples of solvents which can be utilized consistent herewith, there are mentioned nitrobenzene, dimethylsulfone, tetramethylenesulfone and also its derivatives, such as 3-methyltetramethylenesulfone, 2,4-dimethyltetramethylenesulfone and dichlorotetramethylenesulfone. Tetramethlyenesulfone and derivatives thereof are especially suitable for carrying out the process according to the invention.

The present invention also envisages the use of mixtures of these solvents, insofar as the latter are compatible. In particular, mixtures of tetramethylenesulfone and its derivatives are desirably used. The reaction is carried out in an essentially anhydrous medium.

The choice of carboxylic acid to be esterified, according to the present invention, will quite obviously depend on the nature of the desired ethyl ester. By way of examples of carboxylic acids which can be esterified within the scope of the present invention, there are mentioned: saturated or unsaturated aliphatic monocarboxylic acids which have up to 20 carbon atoms in the molecule, and which are either unsubstituted or bear substituents, especially one or more halogen atoms, in particular acetic, propionic, butyric, isobutyric, hexanoic, monochloroacetic, dichloroacetic, bromoacetic, chloropropionic, acrylic and methacrylic acids. The invention also envisages the use of aromatic monocarboxylic acids, in particular benzoic and toluic acids, alicyclic acids as naphthenic acids, aliphatic dicarboxylic acids having from 3 to 6 carbon atoms in the molecule, in particular succinic and adipic acids, and aromatic dicarboxylic acids, in particular the phthalic acids. The reaction is preferably carried out utilizing acetic acid.

The catalysts to be employed within the scope of the invention are characteristically inorganic acids or strong organic acids. By way of examples of catalysts which are advantageously used within the scope of the present invention, there are mentioned: sulfuric acid, alkanesulfonic acids, in particular methanesulfonic acid and its higher homologues up to $C_6$, arylsulfonic acids, in particular benzenesulfonic acid p-toluenesulfonic acid, benzenedisulfonic acids and naphthalenedisulfonic acids, fluorosulfonic acid, and alkylhalogenosulfonic acids, in particular polyfluoroalkanesulfonic acids and perfluoroalkanesulfonic acids and perfluoroalkanesulfonic acids having at most 8 carbon atoms in the molecule.

The invention also envisages the use, as catalysts, of the aforesaid acids in the form of their lower alkyl esters having, in particular, from 1 to 4 carbon atoms in the alkyl radical, and more particularly in the form of their ethyl esters.

The invention also envisages the use of mixtures of the foregoing catalysts.

According to a preferred embodiment of the invention, the acid catalyst used is a perfluoroalkanesulfonic acid or a mixture of several perfluoroalkane sulfonic acids which have at most 8 carbon atoms in the molecule and, if necessary, are partially or totally in the form of their lower alkyl esters having, in particular, from 1 to 4 carbon atoms in the alkyl radical, the ethyl esters being more particularly envisaged.

Trifluoromethanesulfonic acid, and/or its lower alkyl esters having, in particular, from 1 to 4 carbon atoms in the alkyl radical, is particularly suitable for carrying out the process according to the invention. Trifluoromethanesulfonic acid, and/or its ethyl ester, is more especially preferred.

The process according to the invention is particularly advantageous for preparing ethyl acetate from ethylene and acetic acid, in particular when tetramethylenesulfone, and/or its derivatives, is used as the solvent. In addition to its efficiency, the present process exhibits the advantage in that all or a portion of the reaction medium can be recycled.

In fact, at the completion of the reaction, the ethyl acetate can be separated by any suitable means and all or part of the catalyst, the solvent and, if necessary, the unreacted acetic acid, can be recycled. It too has been shown, consistent herewith, that the efficiency of the process in question is essentially unaffected by the fact that all or part of the catalyst and of the solvent originates from a recycling operation. At the completion of a first operation, the ethyl acetate formed can be separated off by any suitable means, with a view to its recovery, and the remaining mixture can be recycled in a subsequent operation, without it being necessary to separate the constituents of the mixture and/or purify them beforehand. The mixture thus obtained essentially contains the catalyst, the solvent and, possibly, the unreacted acetic acid.

When, in a subsequent operation, ethylene is reacted with this mixture in the presence of acetic acid, an additional amount of ethyl acetate is obtained in a yield which is approximately equal to that attained in the first operation, even if several successive recycling operations are carried out.

According to a preferred embodiment of the invention, there is added, during the recycling operation, an amount of fresh acetic acid which approximately corresponds to the amount converted in the previous operation.

The fresh acetic acid can be introduced into the recycling stream or, for example, directly into the reactor.

According to the process of the invention, ethyl esters are obtained by reacting ethylene, in the liquid phase, with a mixture essentially comprising at least one carboxylic acid, at least one acid catalyst, and at least one solvent, the necessary characteristics of which have been outlined hereinabove.

According to another preferred embodiment of the invention, the relative amount of solvent, as defined by the molar fraction f of solvent in the mixture of solvent and carboxylic acid, namely, the acid constituting the acid part of the desired ethyl ester, is greater than or equal to 0.4.

The amount of catalyst to be introduced into the reaction medium is not critical. In general, an amount of between 0.05 and 2 mols per liter of reaction mixture is satisfactory. This amount is preferably between 0.1 and 1 mol/liter.

The ethylene pressure must be greater than atmospheric pressure. A pressure of between 20 and 60 bars is particularly suitable for carrying out the invention.

The reaction temperature is not critical. However, below 100° C., the reaction rate is slow, whereas, above 200° C., the appearance of secondary products, due to decomposition, is observed. The temperature will preferably be between 130° and 160° C.

In order to further illustrate the present invention and the advantages thereof, the following specific examples are given, it being understood that same are intended only as illustrative and in nowise limitative.

EXAMPLES

Examples 1 to 7

Acetic acid, tetramethylenesulfone (TMS) and a catalyst were introduced into a 250 cm$^3$ Hastelloy C bomb reactor. The mixture was heated to the selected temperature in an oven, with lengthwise agitation. Ethylene was then charged into the reactor. The ethylene pressure was 40 bars, unless otherwise indicated. The reaction was stopped after 4 hours, unless otherwise indicated. The results obtained, which are expressed as the degree of conversion of the acid into ethyl acetate (DC), andalso the particular conditions, are reflected in Table I below; the last column indicates the degree of conversion of the acid into ethyl acetate (DC$_0$) which is obtained in the absence of tetramethylenesulfone, all other conditions being the same.

In these examples, and also in all following examples, the selectivity with respect to the desired ester was on the order of 100%.

TABLE I

| Example No. | CATALYST Nature | mol/liter | TMS in mol | Acetic acid in mol | Temperature °C. | DC% | DC$_0$% |
|---|---|---|---|---|---|---|---|
| 1 | $H_2SO_4$ | 0.925 | 0.821 | 0.353 | 150 | 33.4 | 3.5 |
| 2 | $CH_3SO_3H$ | 1.00 | 0.822 | 0.345 | 160 | 16.5 | ε |
| 3 | ⌬(SO$_3$H)$_2$ | 0.50 | 0.793 | 0.342 | 160 | 50.7 | 4.9 |
| 4 | $CH_3SO_3H$ | 0.326 | 0.6 | 0.6 | 150 | 75.0 | 9.3 |
| 5$^{(x)}$ | $C_6F_{13}SO_3H$ | 0.158 | 0.604 | 0.601 | 160 | 54.2 | — |
| 6$^{(xx)}$ | resin | 10 g | 0.60 | 0.608 | 160 | 25.0 | — |
| 7 | $CH_3SO_3C_2H_5$ | 0.322 | 0.60 | 0.60 | 150 | 80 | — |

$^{(x)}$This experiment was carried out using an ethylene pressure of 30 bars for 2 hours, 30 minutes.
$^{(xx)}$This experiment was carried out using 10 g of a perfluorosulfonic acid resin marketed under the trademark NAFION (duration of the experiment: 3 hours). This resin contains copolymers of perfluoroethylene with a perfluorovinyl ether, the said ether bearing sulfonic acid groups.
In the last column (DC$_0$%) ε means undeterminable (too small); - means non-determined.

Examples 8 to 14

Acetic acid, trifluoromethanesulfonic acid and a solvent were introduced in accordance with the general process described above.

The particular conditions and also the results obtained are included in Table II below, in which:
MTMS denotes 3-methyltetramethylenesulfone
DMTMS denotes 2,4-dimethyltetramethylenesulfone
DMS denotes dimethylsulfone
NG denotes nitrobenzene
TMS denotes tetramethylenesulfone

TABLE II

| Example No. | (CF$_3$SO$_3$H) (mol/liter) | SOLVENT Nature | SOLVENT Mol | Acetic acid (mol) | Pressure (bars) | Temperature (°C.) | Duration (hrs.) | DC (%) |
|---|---|---|---|---|---|---|---|---|
| 8  | 0.313 | MTMS  | 0.607 | 0.598 | 40 | 150 | 4 | 71.2 |
| 9  | 0.324 | DMTMS | 0.501 | 0.498 | 40 | 150 | 4 | 55.3 |
| 10 | 0.335 | NB    | 0.798 | 0.335 | 40 | 150 | 4 | 47.5 |
| 11 | 0.345 | DMS   | 0.60  | 0.765 | 40 | 150 | 4 | 35.0 |
| 12 | 0.32  | TMS   | 0.578 | 0.58  | 40 | 140 | 3 | 36.5 |
| 13 | 0.164 | TMS   | 0.59  | 0.595 | 60 | 150 | 3 | 47.7 |
| 14 | 0.32  | TMS   | 0.578 | 0.578 | 40 | 160 | 2 | 69.5 |

Examples 15 to 17

Various ethyl esters (RCOOC$_2$H$_5$) were prepared by reacting ethylene with a carboxylic acid (RCOOH) in accordance with the general process described above, the reaction being carried out in tetramethylenesulfone in the presence of trifluoromethanesulfonic acid as the catalyst. The particular conditions and the results obtained after a reaction time of 4 hours are given in Table III below:

TABLE III

| Example No. | CF$_3$SO$_3$H in mol/liter | TMS in mol | Carboxylic acid Nature | Carboxylic acid Mol | T in °C. | P in bars | % DC of RCOOC$_2$H$_5$ |
|---|---|---|---|---|---|---|---|
| 15 | 0.306 | 0.603 | propionic | 0.6   | 150 | 40 | 83.7 |
| 16 | 0.295 | 0.50  | hexanoic  | 0.497 | 150 | 20 | 72.4 |
| 17 | 0.308 | 0.613 | benzoic   | 0.4   | 140 | 40 | 100.0 |

Examples 18 to 22

Various experiments relating to the preparation of ethyl acetate were carried out, in accordance with the general process described above, by reacting ethylene (pressure: 40 bars) with acetic acid in a medium containing varying proportions of tetramethylenesulfone, the catalyst being trifluoromethanesulfonic acid. The reaction temperature was 150° C. and the reaction time was four (4) hours.

The particular conditions and also the results obtained are shown in Table IV below, in which f denotes the ratio of the number of mols of solvent to the total number of mols of solvent and of carboxylic acid.

TABLE IV

| Example No. | Catalyst in mol/liter | Solvent in mol | Acetic acid in mol | f | DC % |
|---|---|---|---|---|---|
| 18   | 0.293 | 0.163 | 1.437 | 0.102 | 14.0 |
| 19   | 0.317 | 0.502 | 1.005 | 0.333 | 37.3 |
| 4    | 0.326 | 0.60  | 0.60  | 0.50  | 75.0 |
| 20   | 0.311 | 0.802 | 0.35  | 0.696 | 100  |
| 21 x | 0.09  | 0.899 | 0.105 | 0.895 | 50.2 |
| 22 xx| 0.319 | 0.60  | 0.60  | 0.5   | 52.0 | x This experiment was carried out at 110° C.
xx This experiment was carried out using an ethylene pressure of 20 bars.

Example 23

44.4 g of acetic acid, 93.3 g of tetramethylenesulfone and 7.0 g of trifluoromethanesulfonic acid were introduced into a 250 cm$^3$ Hastelloy C bomb reactor.

The mixture was heated to a temperature of 150° C. by means of an oven, with lengthwise agitation. The ethylene was then charged into the reactor under a pressure of 40 bars. The reaction was stopped after 3 hours.

The ethyl acetate formed was then distilled under reduced pressure. This yields: 45.0 g of ethyl acetate and 111.8 g of a distillation residue essentially consisting of tetramethylenesulfone, trifluoromethanesulfonic acid and unreacted acetic acid.

Examples 24 to 29

Using the method of operation described for Example 23, but introducing the distillation residue (111.8 g) obtained in Example 23, a second operation was carried out under the same conditions of temperature, pressure and time, 35.5 g of fresh acetic acid being added. At the end of the operation, the ethyl acetate formed was distilled and the distillation residue was used to carry out the operation of Example 25; the operations corresponding to Examples 24 to 29 were carried out in accordance with this same principle.

For each example, Table V below shows the amount of recycled distillation residue originating from the previous operation (recycling), the amount of fresh acetic acid added (acid) and also the mass of distilled ethyl acetate (M) at the end of each operation.

TABLE V

| EXAMPLES | 24 | 25 | 26 | 27 | 28 | 29 |
|---|---|---|---|---|---|---|
| Acid (g)      | 35.5  | 32.5  | 31.8  | 27.2  | 28.7  | 29.1 |
| Recycling (g) | 111.8 | 114.1 | 115.6 | 119.7 | 116.9 | 115.7 |
| M (g)         | 46.1  | 42.9  | 38.5  | 41.2  | 41.0  | 39.5 |

While there have been described and pointed out the fundamental novel features of the invention as applied to the preferred embodiments, those skilled in the art will appreciate that various modifications, changes and omissions can be made without departing from the spirit of the invention. It is the intention, therefore, to be limited only by the scope of the following claims.

What is claimed is:

1. In a process for the preparation of an ethyl carboxylate, in the liquid phase, from ethylene under pressure and at least one carboxylic acid, in the presence of an effective amount of acid catalyst, the improvement which comprises conducting the reaction in an essentially anhydrous medium comprising at least one solvent selected from the group consisting of nitrobenzene, dimethylsulfone, tetramethylenesulfone, dichloro-tetramethylenesulfone, 3-methyltetramethylenesulfone and 2,4-dimethyltetramethylenesulfone.

2. The process as defined by claim 1, wherein the carboxylic acid is selected from the group comprising saturated or unsaturated aliphatic acids which have up to 20 carbon atoms, saturated or unsaturated halogen substituted aliphatic acids which have up to 20 carbon atoms, and benzoic, toluic, napthenic, succinic, adipic and phthalic acids.

3. The process as defined by claim 2, the carboxylic acid being selected from the group consisting of acetic, propionic, butyric, isobutyric, hexanoic, monochloroacetic, dichloroacetic, bromoacetic and chloropropionic acids.

4. The process as defined by claim 3, the carboxylic acid being acetic acid.

5. The process as defined by claim 1, wherein the solvent is selected from the group comprising tetramethylenesulfone, 3-methyltetramethylenesulfone, 2,4-dimethyltetramethylenesulfone, and dichloro-tetramethylenesulfone, and mixtures thereof.

6. The process as defined by claim 1 for the preparation of ethyl acetate by reacting ethylene under pressure, in the liquid phase, with a mixture containing acetic acid, at least one acid catalyst, and at least one solvent selected from the group comprising tetramethylenesulfone and 3-methyltetramethylenesulfone, 2,4-dimethyltetramethylenesulfone, and dichloro-tetramethylenesulfone, the improvement which comprises recovering the ethyl acetate as formed and recycling any remaining reaction mass.

7. The process as defined by claim 6, said recycle comprising the catalyst, the solvent and unreacted acetic acid.

8. The process as defined by claim 6 or 7, wherein during recycling, there is added to the reaction mass an amount of fresh acetic acid approximately corresponding to the amount of acid already converted.

9. The process as defined by claim 1, wherein the catalyst is selected from the group comprising sulfuric acid, alkanesulfonic acids having at most 6 carbon atoms, benzenesulfonic acid, p-toluenesulfonic acid, benzenedisulfonic acids, naphthalenedisulfonic acids, perfluoroalkanesulfonic acids having at most 8 carbon atoms, the lower alkyl esters thereof, and mixtures thereof.

10. The process as defined by claim 9, wherein the catalyst is selected from the group consisting of perfluoroalkanesulfonic acids having at most 8 carbon atoms, the lower alkyl esters thereof, and mixtures thereof.

11. The process as defined by claim 9, wherein the catalyst is selected from the group comprising trifluoromethanesulfonic acid, lower alkyl esters thereof, and mixtures thereof.

12. The process as defined by claim 9, wherein the catalyst is partially or totally in ester form.

13. The process as defined by claim 12, wherein the catalyst is partially or totally in the form of the ethyl ester.

14. The process as defined by claim 1, wherein the molar fraction f of the solvent is greater than or equal to 0.4.

15. The process as defined by claim 1 wherein the amount of catalyst employed is between 0.05 and 2 mols per liter of reaction mixture.

16. The process as defined by claim 15, wherein the amount of catalyst is between 0.1 and 1 mol per liter of mixture.

17. The process as defined by claim 1, wherein the ethylene pressure is between 20 and 60 bars.

18. The process as defined by claim 1, wherein the reaction temperature is between 100° and 200° C.

19. The process as defined by claim 18, wherein the reaction temperature is between 130° and 160° C.

* * * * *